United States Patent [19]
Cooper et al.

[11] 3,963,695
[45] June 15, 1976

[54] TETRADEOXYNEAMINE AND DERIVATIVES THEREOF

[75] Inventors: David J. Cooper, Downingtown, Pa.; Francis R. Pfeiffer, Cinnaminson, N.J.

[73] Assignee: SmithKline Corporation, Philadelphia, Pa.

[22] Filed: Dec. 19, 1974

[21] Appl. No.: 534,247

[52] U.S. Cl. .............................. 260/210 AB; 424/180
[51] Int. Cl.$^2$ ......................................... C07H 15/22
[58] Field of Search .................... 260/210 AB, 211 R

[56] References Cited
UNITED STATES PATENTS 3,872,080  3/1975  Daniels ........................ 260/210 AB

OTHER PUBLICATIONS

Fujisawa et al., "Jour. Antibiotics", vol. XXVII, No. 9, 1974, pp. 677–681.

*Primary Examiner*—Johnnie R. Brown
*Attorney, Agent, or Firm*—Stuart R. Suter; William H. Edgerton; Alan D. Lourie

[57] ABSTRACT

Novel deoxy derivatives of neamine are prepared and disclosed as antibacterial agents.

6 Claims, No Drawings

TETRADEOXYNEAMINE AND DERIVATIVES THEREOF

This invention relates to novel compounds in the aminoglycoside group of antibiotics; in particular, to tetradeoxyneamine and derivatives thereof.

BACKGROUND

Aminoglycosides are an important group of antibiotic compounds which have particularly useful activity against organisms that are resistant to many antibacterial agents. Many aminoglycosides have as a major structural feature the pseudodisaccharide neamine which has the following structural formula:

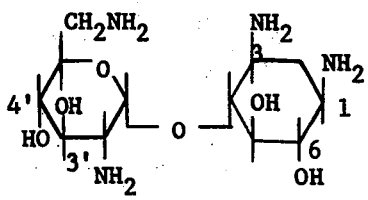

Some aminoglycosides are comprised of deoxy derivatives of neamine in which one or two hydroxy groups are not present. For example, the various members of the gentamicin group contain 3',4'-dideoxyneamine derivatives and tobramycin contains 3'-deoxyneamine. In addition 4'-deoxybutirosin has been reported. Natural aminoglycosides containing other deoxyneamines have not been reported to the best of our knowledge.

SUMMARY OF THE INVENTION

The compounds of this invention are represented by the following structure:

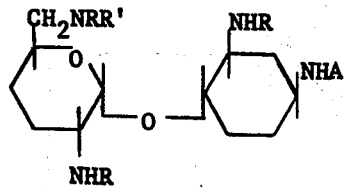

where
R is hydrogen or a removable amino protecting group;
R' is hydrogen, methyl or ethyl; and
A is R.

The removable protecting groups are any group used in the arts of carbohydrate or peptide synthesis to protect an amino group during chemical reactions. These include such amino protecting groups as acetyl, tosyl, benzoyl, mesyl, methylsulfate, dichloroacetyl, trichloroethoxycarbonyl, benzyloxycarbonyl, t-butoxycarbonyl, ethoxycarbonyl, methoxycarbonyl, dinitrophenyl, enamine adduct of dimedone and the like. Particularly useful protecting groups are the methoxycarbonyl, ethoxycarbonyl and benzyloxycarbonyl groups. The choice of the proper protecting group is within the ordinary ability of one skilled in the art and is based on various factors such as subsequent reactions conditions, and desirable conditions for removal.

The butyryl, propionyl and valeryl derivatives within the definition of A given above have an asymmetric carbon atom which gives rise to optical isomers. The diastereomers having the L-configuration are preferred; however, those having the D-configuration and diastereomeric mixtures are within the scope of the invention.

Also within the scope of this invention are the nontoxic pharmaceutically acceptable acid addition salts of the compounds which have a free amino group. Such salts, prepared by well known methods, are formed from both inorganic and organic acids such as maleic, fumaric, benzoic, ascorbic, pamoic, succinic, bismethylenesalicyclic, methanesulfonic, ethanedisulfuric, acetic, oxalic, propionic, tartaric, salicyclic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric, and nitric acids. In addition, the salts of the compounds may be converted back to the free base compounds by standard chemical methods.

The compounds of this invention are prepared from neamine, a compound readily available from the hydrolysis of neomycin by published methods. Scheme I sets forth in detail one particular series of reactions which can be used to prepare one compound within the scope of the invention. Neamine is reacted with methyl chloroformate by published methods to give tetra-N-methoxycarbonylneamine (2) [J. Antibiotics, 24 711 (1971)]. Treatment of this compound with mesyl chloride in the presence of base gives tetra-N-methoxycarbonyl-tetra-O-mesylneamine (3). Reaction of this compound with zinc and sodium iodide by known methods gives the dieno compound 4. Reduction of the double bonds and removal of the methoxycarbonyl protecting groups gives tetradeoxyneamine (6).

Compounds wherein R is methyl are prepared as outlined in Scheme II. Tetradeoxyneamine is reacted with one equivalent of N-benzyloxycarbonyloxysuccinimide to to give the 6'-N-benzyloxycarbonyl derivative 7 which is reduced with lithium aluminum hydride to give 6'-methyl-3',4',5,6-tetradeoxyneamine.

Compounds of this invention wherein R and A are other than an amino protecting group have antibacterial activity against a variety of organisms. For example, 3',4',5,6-tetradeoxymeamine sulfate (6) gave minimum inhibitory concentrations (MIC) in the range of 6.3 to greater than 200 mg/ml against a group of 15 common Gram-positive and Gram-negative organisms. Compounds of this invention wherein A and/or R are an amino protecting group are useful for preparing the compounds of this invention which have antibacterial activity.

The compounds with antibacterial activity can be used in aqueous solution to sterilize glassware, instruments and the like. They may also be formulated in a similar manner as other known aminoglycosides and used to prevent or treat bacteria infections in animals including man.

SCHEME I

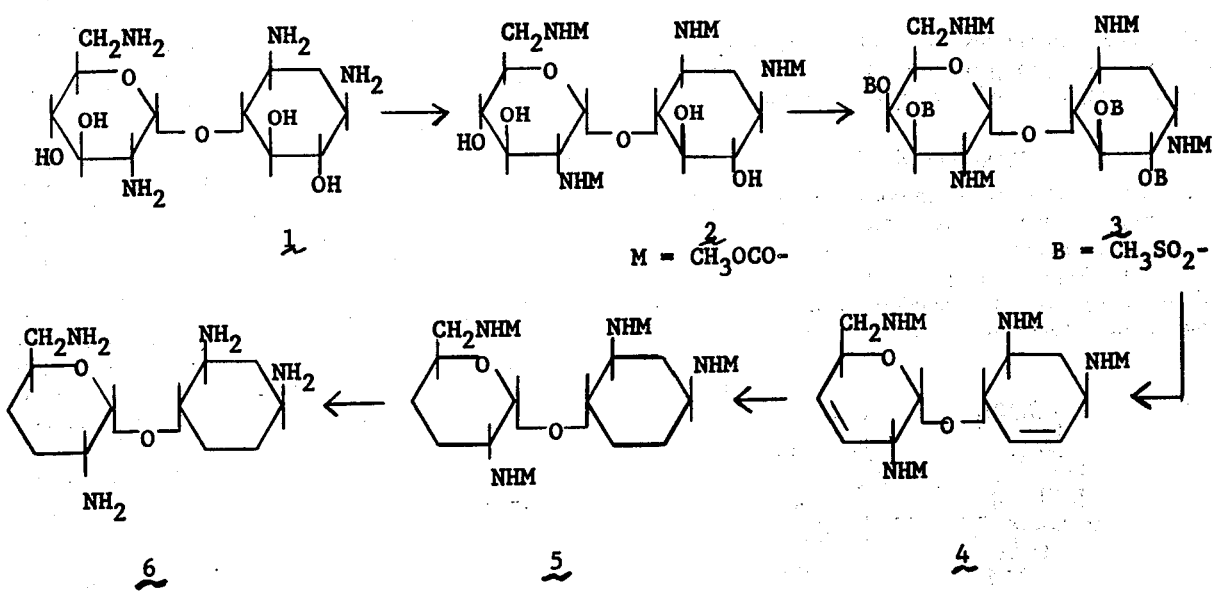

SCHEME II and III

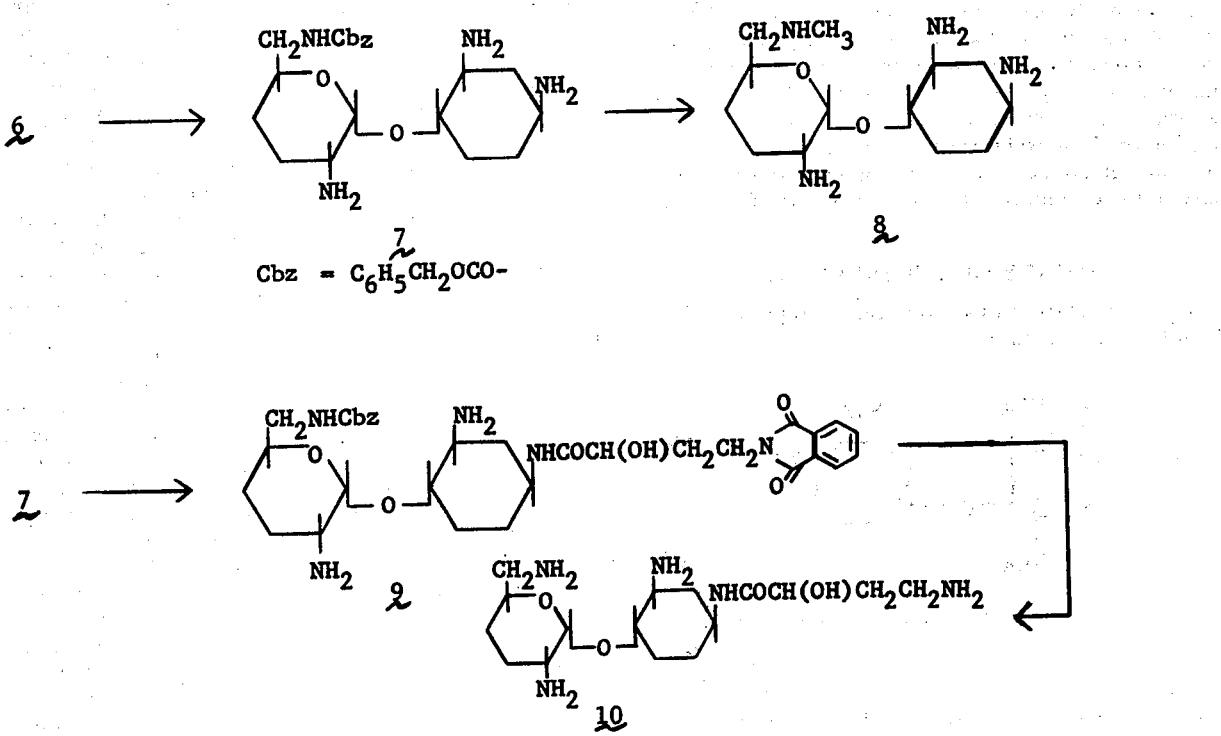

The amount administered to a human in need of treatment depends on the age, size and condition of the person as well as the severity and type of infection. In general, daily dosages are 15 mg/kg, usually administered as two 7.5 mg/kg doses. Other dosage determinations and regiments are within the ability of those skilled in the art.

The following examples illustrate the invention but are not to be construed as limiting the scope thereof. Temperatures are in degrees centigrade unless otherwise stated.

EXAMPLE 1

Neamine is reacted with methyl chloroformate in aqueous acetone at pH 8.5 to give tetra-N-methoxycarbonylneamine (2).

A solution of tetra-N-methoxycarbonylneamine (2.0 g, 3.6 mmol) in dry pyridine (25 ml) is cooled in an ice bath and treated with mesyl chloride (2.1 g, 18.3 mmol). The reaction is heated to 40°C for 6 hours and then quenched by pouring into ice water. The aqueous solution is acidified with HCl and extracted with ethyl acetate. The extracts are washed with dilute HCl, water, cold saturated $NaHCO_3$ and water and then dried and evaporated to give 3′,4′,5,6-tetra-O-mesyl-tetra-N-methoxycarbonylneamine (3); mp 162°–5°.

A suspension of the above tetra-O-mesyl derivative (8.4 g, 9.7 mmol), dry sodium iodide (30 g, 0.2 mmol), zinc dust (13 g) and molecular sieves (1 g) in dry dimethylformamide (75 ml) is heated at 140° for 2 hours. The partially cooled reaction mixture is filtered and the collected inorganic material is washed with ethyl acetate. The filtrate is diluted with cold brine (1.5 l) and the aqueous phase is separated and extracted with ethyl acetate. The combined organic phases are washed with water, dried and concentrated to give 3′,4′,5,6-tetradeoxy-3′,5-dieno-tetra-N-methoxycarbonylneamine (4).

The above dieno derivative (1.7 g) is hydrogenated in methanol (100 ml) with 10% Pd on carbon (1.5 g) at 60 psi for 18 hours. The mixture is filtered and the filtrate is concentrated. The product is chromatographed on a "Florisil" column (50 g) with a gradient of 5% to 15% acetone in ethyl acetate as eluant to give 3′,4′,5,6-tetradeoxy-tetra-N-methoxycarbonylneamine (5) which is recrystallized from acetone-ether; mp 185°–93°, $[\alpha]_D^{25}$ + 96.1 ($c$ 1, $CHCl_3$).

A solution of the above product (870 mg) in dioxane is warmed to 80° and then hot 1N $Ba(OH)_2$ (50 ml) is added. The resulting solution is refluxed for 18 hours under a nitrogen atmosphere and then cooled. The solution is treated with $CO_2$ until the precipitation of $BaCO_3$ is completed which is then filtered off. The filtrate is concentrated and the residue is chromatographed on a polymethacrylic acid ion exchange resin ["Amberlite CG-50"($NH_4^+$)] column (30 × 2.5 cm). The column is eluted with water (2 l) and washed with one liter each of 0.2 N $NH_4OH$, 0.5 N $NH_4OH$, and 1N $NH_4OH$ and 1.5 liter of 1.5 N $NH_4OH$. The product-containing homogeneous fractions, mostly from the 1.5 N $NH_4OH$ eluant, are combined, acidified to pH 3.5 with dilute $H_2SO_4$, and treated with charcoal. The product, 3′,4′,5,6-tetradeoxyneamine sulfate (6), is precipitated by addition of an equal volume of methanol. The product is dissolved in water and lyophilized; mp 262°–263°, $[\alpha]_D^{25}$ + 78.3 ($c$ 1, $H_2O$).

EXAMPLE 2

A solution of 3′,4′,5,6-tetradeoxyneamine sulfate (516 mg, 2 mmol) in water (15 ml) and tetrahydrofuran (10 ml) is cooled in an ice bath and then a solution of N-benzyloxycarbonyloxysuccinimide (520 mg, 2.1 mmol) in tetrahydrofuran (5 ml) is added dropwise over a period of one hour. The reaction is stirred at 0° to 5° for 18 hours and at room temperature for 6 hours. The solvent is removed and the residue is chromatographed on polymethacrylic acid ion exchange resin ["Amberlite CG-50" ($NH_4^+$)] with a gradient of ammonium hydroxide as eluant. The homogeneous fractions from 1.0 to 1.5 N $NH_4OH$ are combined and evaporated to give 6′-benzyloxycarbonyl-3′,4′,5,6-tetradeoxyneamine (7); $[\alpha]_D^{25}$ + 82 ($c$ 1, 50% $H_2O$ in methanol).

EXAMPLE 3

6′-Benzyloxycarbonyl-3′,4′,5,6-tetradeoxyneamine is refluxed with $LiAlH_4$ in dry dimethoxyethane and then treated with NaOH to give 6′-N-methyl-3′,4′,5,6-tetradeoxyneamine (8).

We claim:
1. A compound of the formula

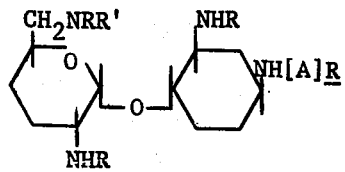

where
R is hydrogen or a removable amino protecting group; and
R′ is hydrogen, methyl or ethyl
or a non-toxic pharmaceutically acceptable salt thereof.

2. A compound as claimed in claim 1 where R is hydrogen, acetyl, tosyl, benzoyl, mesyl, methylsulfate, dichloroacetyl, trichloroethoxycarbonyl, benzyloxycarbonyl, t-butoxycarbonyl, ethoxycarbonyl, methoxycarbonyl, dinitrophenyl, or dimedone adduct.

3. A compound as claimed in claim 2 wherein R′ is hydrogen.

4. A compound as claimed in claim 3 where R is hydrogen, ethoxycarbonyl, methoxycarbonyl, or benzyloxycarbonyl.

5. A compound as claimed in claim 4 being the compound tetra-N-methoxycarbonyl-3′,4′,5,6-tetradeoxyneamine.

6. A compound as claimed in claim 4 being the compound 3′,4′,5,6-tetradeoxyneamine.

* * * * *

UNITED STATES PATENT AND TRADEMARK OFFICE
CERTIFICATE OF CORRECTION

PATENT NO. : 3,963,695
DATED : June 15, 1976
INVENTOR(S) : David J. Cooper and Francis R. Pfeiffer It is certified that error appears in the above-identified patent and that said Letters Patent are hereby corrected as shown below:

Columns 3 and 4: "SCHEME II and III" should read -- SCHEME II

Columns 3 and 4: delete Scheme III which is the series of reactions which converts 7 into compounds 9 and 10

Column 6: within claim 1 the structure should read

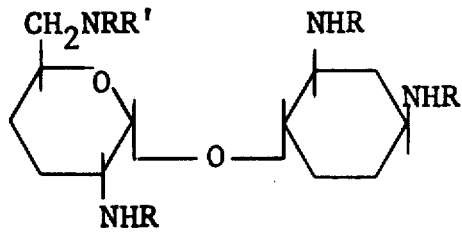

Signed and Sealed this

Twenty-eighth Day of September 1976

[SEAL]

Attest:

RUTH C. MASON
*Attesting Officer*

C. MARSHALL DANN
*Commissioner of Patents and Trademarks*